United States Patent
Virtanen et al.

(10) Patent No.: US 9,738,862 B2
(45) Date of Patent: Aug. 22, 2017

(54) BIOREACTOR APPARATUS

(71) Applicant: MAA-JA ELINTARVIKETALOUDEN TUTKIMUSKESKUS, Jokioinen (FI)

(72) Inventors: Yrjo Virtanen, Somero (FI); Vesa Joutsjoki, Jokioinen (FI)

(73) Assignee: LUONNONVARAKESKUS, Helsinki (FI)

( * ) Notice: Subject to any disclaimer, the term of this patent is extended or adjusted under 35 U.S.C. 154(b) by 161 days.

(21) Appl. No.: 14/441,009

(22) PCT Filed: Nov. 6, 2013

(86) PCT No.: PCT/FI2013/051043
§ 371 (c)(1),
(2) Date: May 6, 2015

(87) PCT Pub. No.: WO2014/072577
PCT Pub. Date: May 15, 2014

(65) Prior Publication Data
US 2015/0299636 A1    Oct. 22, 2015

(30) Foreign Application Priority Data

Nov. 7, 2012   (FI) ................................. 20126162

(51) Int. Cl.
*C12M 1/06* (2006.01)
*B01F 7/00* (2006.01)
(Continued)

(52) U.S. Cl.
CPC ......... *C12M 27/02* (2013.01); *B01F 7/00975* (2013.01); *B01F 7/16* (2013.01);
(Continued)

(58) Field of Classification Search
CPC .......... B01F 2015/062; B01F 15/00071; B01F 15/00175; B01F 15/00389;
(Continued)

(56) References Cited

U.S. PATENT DOCUMENTS 2,206,421 A   7/1940 Muehlhofer
3,373,802 A * 3/1968 Mansson ............... F25D 31/003
                                                     165/109.1
(Continued)

FOREIGN PATENT DOCUMENTS

CN   201180133 Y   1/2009
CN   201737933 U   2/2011
(Continued)

OTHER PUBLICATIONS

Supplementary European Search Report, Application No. EP 13 85 3258, Jul. 5, 2016, 3 pages.
(Continued)

*Primary Examiner* — Michael Hobbs
(74) *Attorney, Agent, or Firm* — Hoffmann & Baron, LLP

(57) ABSTRACT

A bioreactor apparatus includes a vessel establishing an interior space environmentally separable from an exterior space outside of the vessel, an agitation system including mixing means arranged in the interior space and drive means adapted to rotate the mixing means. The drive means includes a drive motor that is arranged in the interior space.

15 Claims, 8 Drawing Sheets

(51) Int. Cl.
*B01F 7/16* (2006.01)
*B01F 15/00* (2006.01)
*B01F 15/06* (2006.01)
*C12M 1/02* (2006.01)
*C12M 1/00* (2006.01)
*C12M 3/00* (2006.01)

(52) U.S. Cl.
CPC .. *B01F 15/00071* (2013.01); *B01F 15/00175* (2013.01); *B01F 15/00389* (2013.01); *B01F 15/00396* (2013.01); *B01F 15/00545* (2013.01); *B01F 15/00662* (2013.01); *B01F 15/00785* (2013.01); *B01F 15/06* (2013.01); *B01F 15/066* (2013.01); *C12M 23/38* (2013.01); *C12M 23/44* (2013.01); *C12M 29/00* (2013.01); *C12M 41/24* (2013.01); *B01F 2015/062* (2013.01); *B01F 2215/0073* (2013.01); *B01F 2215/0431* (2013.01); *B01F 2215/0472* (2013.01)

(58) Field of Classification Search
CPC ......... B01F 15/00396; B01F 15/00545; B01F 15/00662; B01F 15/00785; B01F 15/06; B01F 15/066; B01F 2215/0073; B01F 2215/0431; B01F 2215/0472; B01F 7/00975; B01F 7/16; C12M 23/38; C12M 23/44; C12M 27/02; C12M 29/00; C12M 41/24
See application file for complete search history.

(56) References Cited

U.S. PATENT DOCUMENTS

| | | |
|---|---|---|
| 3,978,918 A | 9/1976 | Nagatomo et al. |
| 4,670,397 A | 6/1987 | Wegner et al. |
| 2002/0146816 A1 | 10/2002 | Vellinger et al. |
| 2005/0032032 A1 | 2/2005 | Pearce, III et al. |
| 2005/0126997 A1 | 6/2005 | Langhans et al. |
| 2010/0248344 A1 | 9/2010 | Schroder et al. |
| 2011/0058448 A1 | 3/2011 | Reif et al. |
| 2012/0009664 A1 | 1/2012 | Buerger |

FOREIGN PATENT DOCUMENTS

| | | |
|---|---|---|
| DE | 2419305 A1 | 11/1974 |
| DE | 3810843 A1 | 10/1989 |
| DE | 4118882 A1 | 12/1992 |
| DE | 102009002925 A1 | 11/2010 |
| EP | 0303149 A2 | 8/1988 |
| EP | 2184099 A2 | 5/2010 |
| EP | 2336346 A1 | 6/2011 |
| GB | 2144767 A | 3/1985 |
| KR | 101033706 B1 | 5/2011 |
| WO | WO2008101124 A1 | 8/2008 |
| WO | WO2008104320 A2 | 9/2008 |

OTHER PUBLICATIONS

International Search Report for corresponding PCT Application No. PCT/FI2013/051043, pp. 1-6, Feb. 21, 2014.
Finnish Search Report for corresponding Finnish Application No. 20126162, pp. 1-2, Jul. 25, 2013.

* cited by examiner

BIOREACTOR APPARATUS

CROSS-REFERENCE TO RELATED APPLICATIONS

This application is a National Stage application of International Application No. PCT/FI2013/051043, filed Nov. 6, 2013, which claims benefit to Finnish Application No. FI 20126162, filed Nov. 7, 2012, which are incorporated by reference herein in their entirety.

BACKGROUND

Field

The invention relates to bioreactor apparatus, comprising a vessel establishing an interior space environmentally separable from an exterior space outside of said vessel, an agitation system comprising mixing means arranged in said interior space and drive means adapted to rotate said mixing means.

Description of the Related Art

There are growing demand for bioreactors where the interior space is isolated from the environment, especially for processes in oxygen-free atmosphere. This is due to the fact that oxygen is a potential inhibitor or impeder of many biological processes and its presence may lead to low-value products or render the product deteriorated.

A problem with known bioreactors is that their sealings are unreliable, especially dynamic sealing between two surfaces moving in relation to each other are problematic in this respect.

SUMMARY

Viewed from a first aspect, there can be provided a bioreactor apparatus comprising a vessel establishing an interior space environmentally separable from an exterior space outside of said vessel, an agitation system comprising mixing means arranged in said interior space and drive means adapted to rotate said mixing means, wherein the drive means comprises a drive motor that is arranged in said interior space.

Thereby a structure of the bioreactor apparatus being easily isolated form the environment may be achieved.

The bioreactor apparatus is characterised by what is stated in the characterising parts of the independent claims. Some other embodiments are characterised by what is stated in the other claims. Inventive embodiments are also disclosed in the specification and drawings of this patent application. The inventive content of the patent application may also be defined in other ways than defined in the following claims. The inventive content may also be formed of several separate inventions, especially if the invention is examined in the light of expressed or implicit sub-tasks or in view of obtained benefits or benefit groups. Some of the definitions contained in the following claims may then be unnecessary in view of the separate inventive ideas. Features of the different embodiments of the invention may, within the scope of the basic inventive idea, be applied to other embodiments.

In one embodiment the drive motor is a hydraulic driven motor. An advantage is that there is no risk for sparking that may cause an explosion within the interior space.

In one embodiment the apparatus comprises a tube heat exchanger arranged in the interior space, the heat exchanger comprising straight or essentially straight tube portions arranged vertically. An advantage is that the tube portions may function not only as heat exchange means but also as static baffles.

BRIEF DESCRIPTION OF THE DRAWINGS

Some embodiments illustrating the present disclosure are described in more detail in the attached drawings, in which.

In the figures, some embodiments are shown simplified for the sake of clarity. Similar parts are marked with the same reference numbers in the figures.

DETAILED DESCRIPTION

Figure 1:
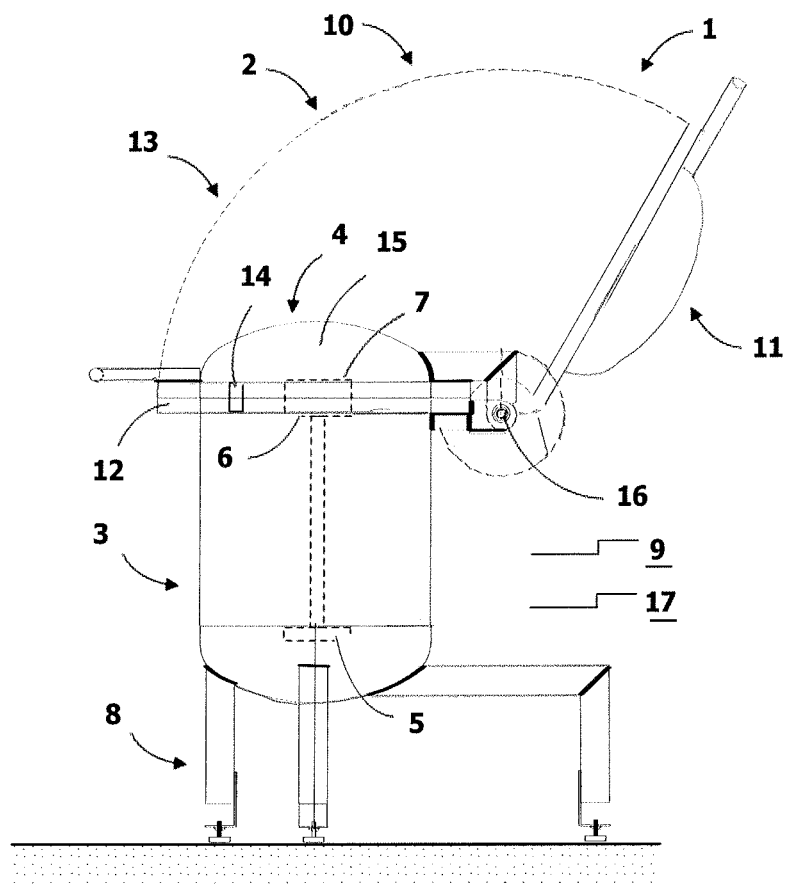
FIG. 1 is a schematic side view of an example apparatus.

FIG. 1 is a schematic side view of an example apparatus.

The bioreactor apparatus 1 comprises a vessel 2 that establishes or surrounds an interior space 3.

The vessel 2 is arranged to environmentally separate the interior space 3 from an exterior space outside of the vessel 2.

The effective capacity of the vessel may be e.g. 1 liter to 100 liters, but it may also be substantially larger, e.g. up to 20 m³ or even more.

The effective capacity means the maximum volume of the matter in liquid-state and/or solid-state that is suitable for treating in the vessel 2. It is to be noted, however, that the matter may further comprise components in gaseous-state.

The bioreactor apparatus 1 further comprises an agitation system 4 that comprises mixing means 5 and drive means 6 adapted to rotate said mixing means 5. The drive means 6 comprises a drive motor 7.

The mixing means 5, the drive means 6 and the drive motor 7 are arranged in said interior space 3, i.e. the vessel 2 separates them from the exterior space outside of the vessel 2.

The vessel 2 may have a cylindrical form as the vessel 2 shown in the Figures. The cylindrical form is usually advantageous due to its inherent ability to assist in creating effective flow patterns in the matter in the interior space 2. Nevertheless, other designs of the vessel 2 are possible.

The vessel 2 may comprise a module structure 10. This means that the interior space 3 may be built up by attaching modules to each other in a detachable way.

The module structure 10 may comprise at least one module 11 that has a flange structure 12 arranged on the exterior surface of said module and the vessel 2.

The flange structure 12 may be manufactured e.g. from same material as the wall of the module 11 and arranged to it by e.g. welding.

The flange structure 12 comprises fixing equipment 13 for receiving fixation means for attachment said module 11 to another module 11.

In the embodiments shown in the Figures the fixing equipment 13 comprises apertures 14 arranged perpendicular to and extending through the flange structure 12. Bolts etc. may be arranged through the apertures 14 in order to attach the module 11.

The aperture 14 may comprise screw thread but it is just an option.

The vessel 2 shown in FIG. 1 comprises a base module 111 that is attached to a lid module 112.

The base module 111 comprises also a bottom part that creates a bottom wall.

The lid module 112 comprises a lid 15 that can be opened for accessing the interior space 3. Therefore the lid module 112 comprises hinge means 16.

The attachment of the base module 111 to the lid module 112 is sealed to gas-tight. The sealing may be realized e.g. by gaskets, sealants and/or sealing plates.

According to an embodiment, the vessel 2 is gas-tight in such an extent that a partial vacuum is allowed to be developed in the interior space 3. The level of the partial vacuum is case-specific and depends on, e.g. the process(es) taking place in the vessel. Thus the apparatus 1 may be used e.g. in vacuum drying processes or biogasification.

The vessel 2 and its modules, if any, may be manufactured from any suitable material. According to an embodiment the material is steel EN 1.4436 or corresponding material.

The modules may comprise couplings, valves etc. that are not shown in the Figures due to sake of clarity.

The mixing means 5 may comprise one or more mixer(s) that is/are suitable for the process in question.

Thus the mixer may comprise radial blades that produce mainly radially directed flows, and/or blades that produces vertically flows either downward or upward direction. Some examples of suitable mixing means are Rushton impellers, pitched-blade mixers and marin-blade mixers.

The drive means 6 comprises a rotating axle in which the mixing means 5 is arranged, and an optional gear means arranged to adjust the rotational speed of the axle on suitable level.

The rotating axle shown in Figures is arranged in an upright position and in the middle line of the vessel 2. According to another embodiment the axle is tilted away from an upright position. The axle may also be arranged in an offset in respect to the middle line of the vessel 2.

The drive motor 7 may be e.g. an electric motor or a hydraulic driven motor. An advantage of the hydraulic driven motor is that there is no risk for sparking. Sparking may cause danger of explosion.

If a hydraulic driven motor is used, a hydraulic pump 17 creating hydraulic pressure needed in the motor may be arranged in the exterior space outside of the vessel 2. Lines or channels conveying hydraulic fluid between the drive motor 7 and the hydraulic pump 17 are reliable to be applied through the wall of the vessel 2 in a gas-tight manner.

An advantage of arranging the drive motor 7 inside the vessel is that the bioreactor apparatus is easily isolated form the environment, because e.g. there is no need for arranging a bearing of the axle to the wall of the vessel. Said bearing is a potential risk for causing leakage, especially when a partial vacuum is applied in the interior space 3.

Another advantage of arranging the drive motor 7 inside the vessel is that thermal energy created by the running drive motor 7 can be utilized in heating of processes or reactions needing added thermal energy. This way a more efficient mixing process may be achieved because a need for inputting thermal energy from outside the apparatus is limited, or even needless.

Reactions and processes taking place in the bioreactor apparatus 1 may have a very narrow temperature range. Thus controlling of the temperature in the interior space 3 is usually needed. For this purpose, the bioreactor apparatus may comprise temperature controlling means 9. According to an embodiment, the temperature controlling means 9 has capability for keeping the temperature of the interior space 3, and thus the temperature of processed matter, below 50° C., preferably below 45° C.

The temperature controlling means 9 may be arranged for controlling not only heat exchanger(s), if any, but also running speed of the drive motor 7. This may be needed because thermal energy created by the drive motor 7 and mixing means rotating in the processed matter can play a major role in heat generation in the vessel 2.

The temperature controlling means 9 may have an ability to change the targeted temperature during the process.

The vessel may be arranged to a support frame 8.

Figure 2:
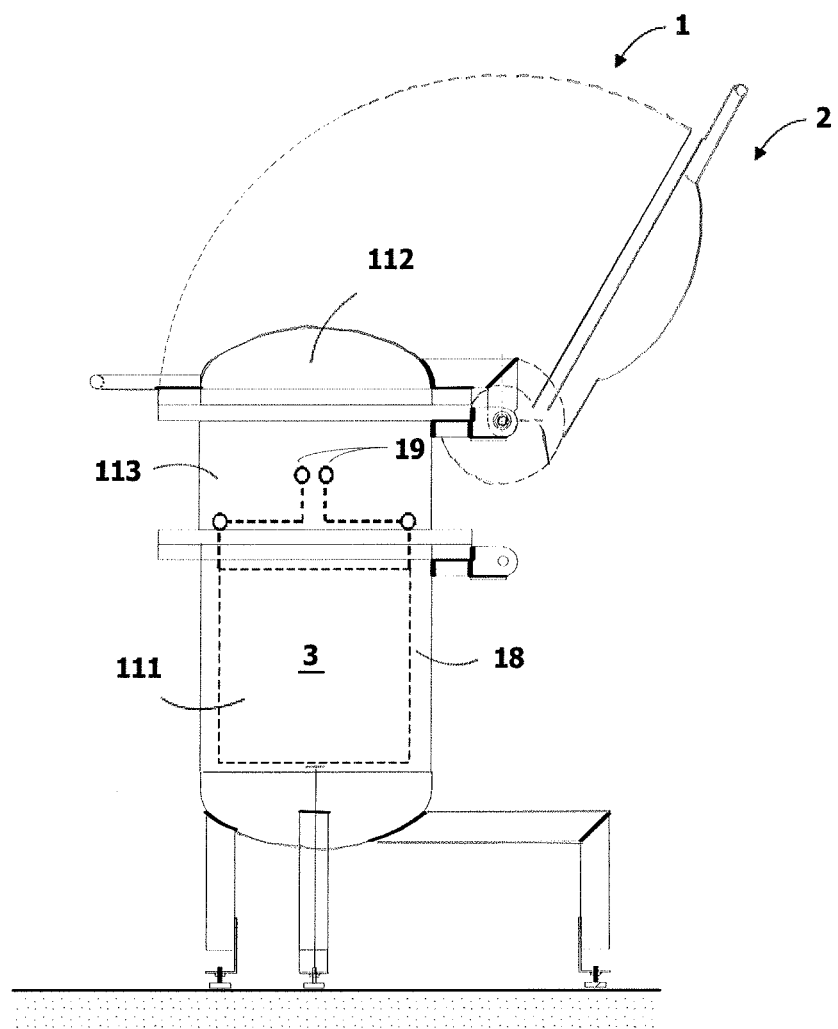
FIG. 2 is a schematic side view of another example apparatus in partial cross-section.

FIG. 2 is a schematic side view of another example apparatus in partial cross-section.

This embodiment comprises a heat exchanger 18 arranged in the interior space 3.

The heat exchanger 18 is now a tube heat exchanger but, of course, another type of heat exchangers may also be utilized in the bioreactor apparatus 1.

Figure 4:
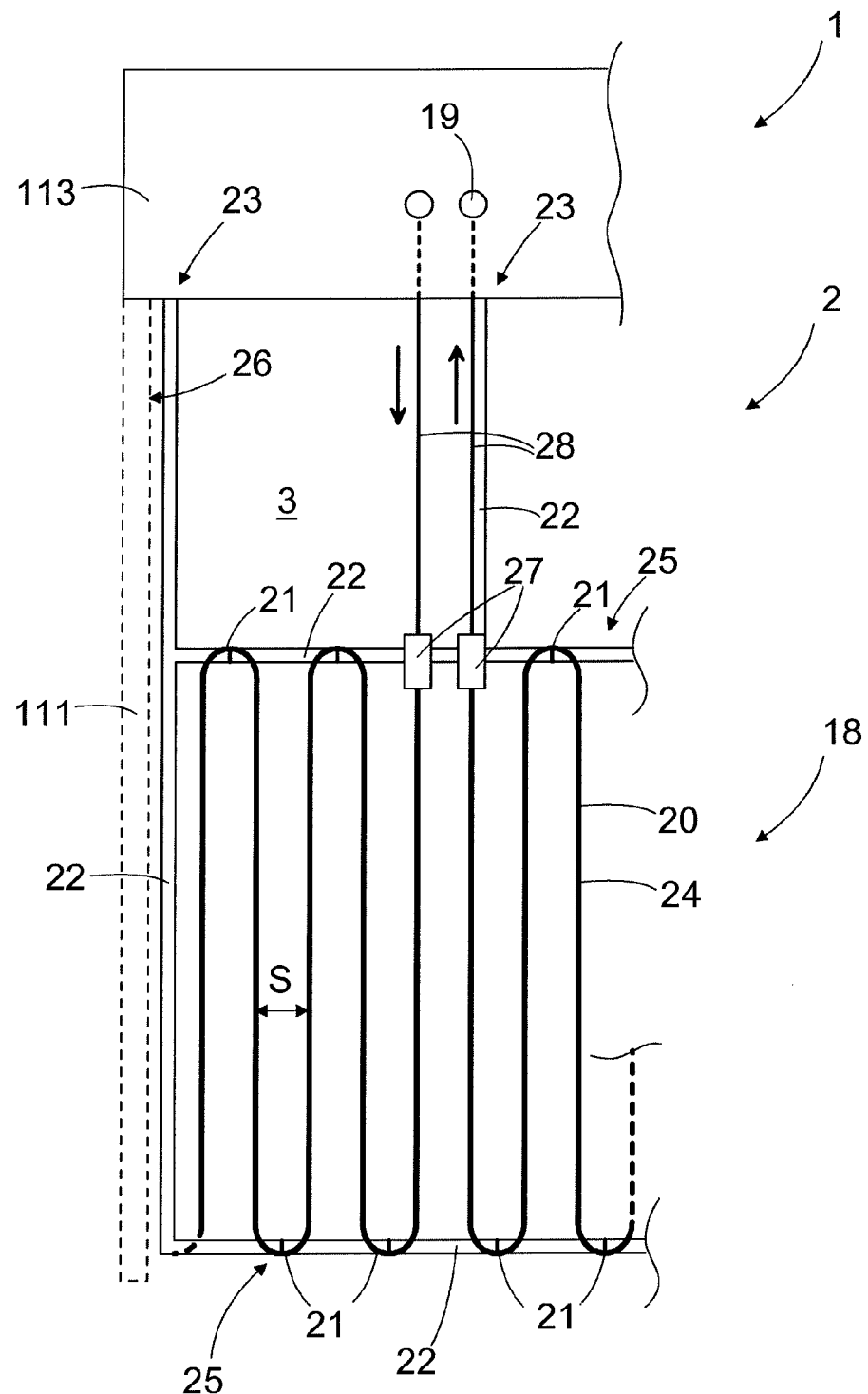
FIG. 4 is a schematic side view of fourth example apparatus in partial cross-section.

An embodiment of the heat exchanger 18 is shown in more detailed way in FIG. 4.

The heat exchanger 18 is detachably fixed in the interior space 3. The feature "detachably fixed" is realized so that the heat exchanger 18 is attached to a heat exchanger module 113.

The heat exchanger module 113 is attached between a base module 111 and a lid module 112 and arranged to establish an annular section of the vessel 2 separating interior space 3 from the exterior space.

The heat exchanger module 113 is detachably fixed to said base module 111 and said lid module 112 by using flange structures 12 thereof.

The majority of the tube portions of the heat exchanger 18 are arranged immediate proximity to the inner surface of the base module 111. Nevertheless, the heat exchanger 18 is preferably not attached to the base module 111. Thanks to this, the heat exchanger 18 can be removed from the vessel 2 just lifting the heat exchanger module 113 out from the apparatus.

Couplings 19 for conveying heat transfer medium in the heat exchanger 18 and out of it are arranged in the annular wall of the exchanger module 113. Said couplings 19 extends through the wall of the exchanger module 113 and they may comprise valves for stopping or adjusting flow of the heat transfer medium.

Temperature controlling means 9 controls the temperature of the interior space 3 and adjust the flow and/or temperature of the heat transfer medium accordingly. The heat transfer medium may comprise liquid and/or vapour, e.g. water and/or water vapour.

The temperature controlling means 9 may be arranged for controlling also running speed of the drive motor 7.

It is to be noted that the heat exchanger module 113 is just an optional part of the heat exchanger arrangement. According to an embodiment, the heat exchanger 18 may be arranged in the base module 111 or lid module 112 or some other part of the vessel 2.

Figure 3:
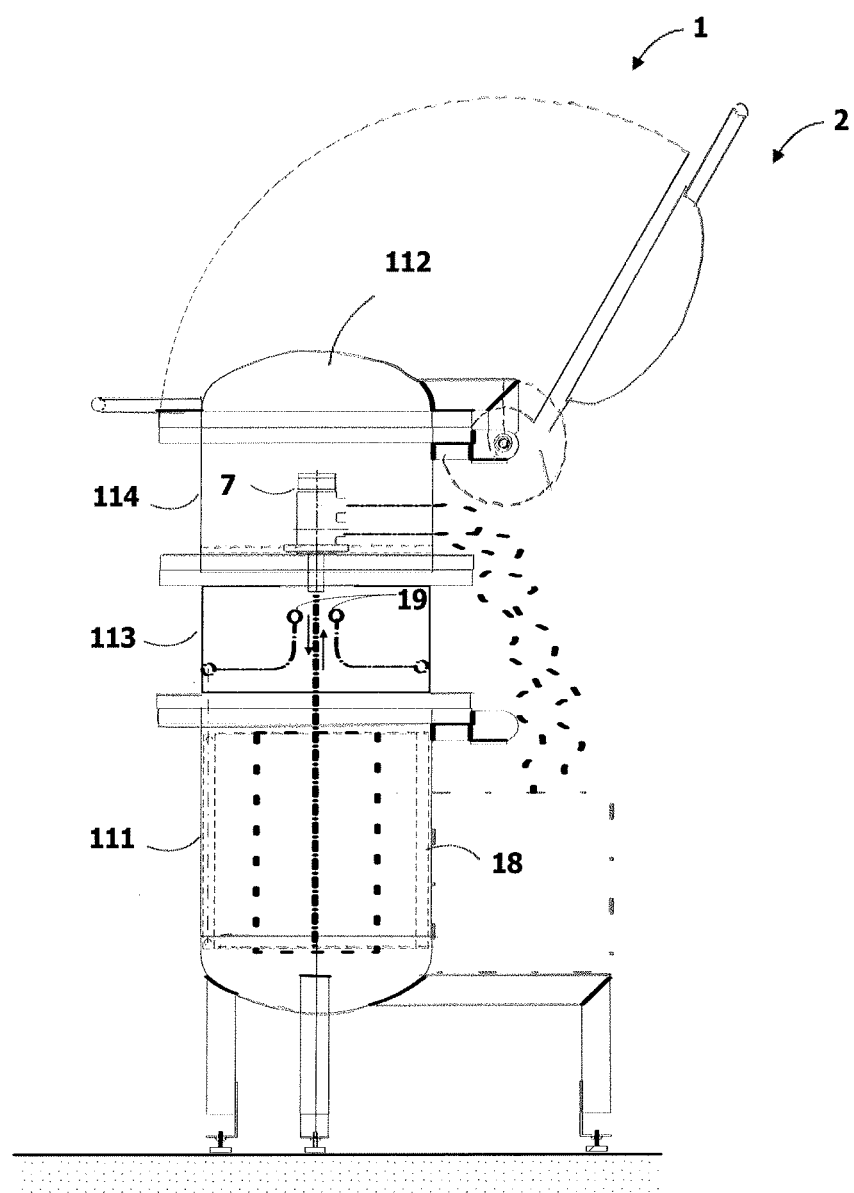
FIG. 3 is a schematic side view of third example apparatus in partial cross-section.

FIG. 3 is a schematic side view of third example apparatus in partial cross-section.

This example apparatus is similar to that shown in FIG. 2 except a motor module 114 that is arranged and detachable fixed between a heat exchanger module 113 and a lid module 112.

The motor module 114 is arranged to establish an annular section of the vessel 2 separating interior space 3 from the exterior space.

The agitation system 4 is attached to the motor module 114. Furthermore, lines, channels, wires etc. needed for running the agitation system 4 are arranged to penetrate the wall of the motor module 114 in a gas-tight manner.

The agitation system 4 can be removed from the apparatus 1 by detaching simply the motor module 114 from the vessel 2.

The interior space 3 is easy to clean up after removing the motor module 114 and the heat exchanger module 113.

FIG. 4 is a schematic side view of fourth example apparatus in partial cross-section. A base module 111 is shown by dashed lines.

The heat exchanger 18 of the apparatus 1 is here a tube heat exchanger. The heat exchanger 18 comprises at least one heat exchanger tube 20 through which a heat transfer medium can be arranged to flow.

The heat exchanger tube 20 comprises straight or essentially straight tube portions 24 arranged at spacing S and parallel to one another and curved tube portions 25 connecting said straight tube portions 24 to form a zigzag tube.

The heat exchanger tube 20 may be manufactured from e.g. steel EN 14404 or similar material. According to an embodiment, the tube is formed by preformed curved pipe portions 25 that are welded to straight tube portions 24.

Said tube portions 24, 25 are preferably arranged immediate proximity to the inner surface 26 of the vessel 2.

The term "immediate proximity" means that the tube portions are either in contact with the inner surface 26 or, preferably, not in contact with said inner surface 26 but very close to it. The latter embodiment may be preferred because heat transfer from the tubes is directed more effective to the matter being mixed.

The straight or essentially straight tube portions 24 are arranged vertically. Said tube portions may function not only as heat exchange means but also as static baffles. The static baffles prevent vortex formation on the surface of the matter being mixed. The vertically arranged tube portions 24 may be effective baffles especially when the mixing means 5 (not shown in FIG. 4) comprises radial blades.

According to another embodiment, the straight or essentially straight tube portions 24 are arranged in horizontal direction in the interior space 2. This kind of heat exchanger 18 may function as effective static baffles especially when the mixing means 5 comprises blades that produces vertically flows either downward or upward direction.

The heat exchanger 18 may also have another construction. The tubes may be arranged in a plate or honeycomb structure made of metal, etc.

The heat exchanger 18 may be mounted to an exchanger framework 22 by fixing elements 21.

The exchanger framework 22 is detachably fixed in the interior space 3. In the embodiment shown in FIG. 4, the exchanger framework 22 is attached to a heat exchanger module 113. Features of the heat exchanger module 113 are discussed in this description relating to FIG. 3.

The heat exchanger tube 20 may be connected to delivery pipes 28 by connectors 27. The opposite end of the delivery pipes 28 are connected to couplings 19 extending through the wall of the exchanger module 113.

The delivery pipes 28 may be manufactured from the same material as the heat exchanger tube 20, or from flexible hose etc. Arrows in FIG. 4 are showing flowing direction of the heat exchange medium.

Figure 5:
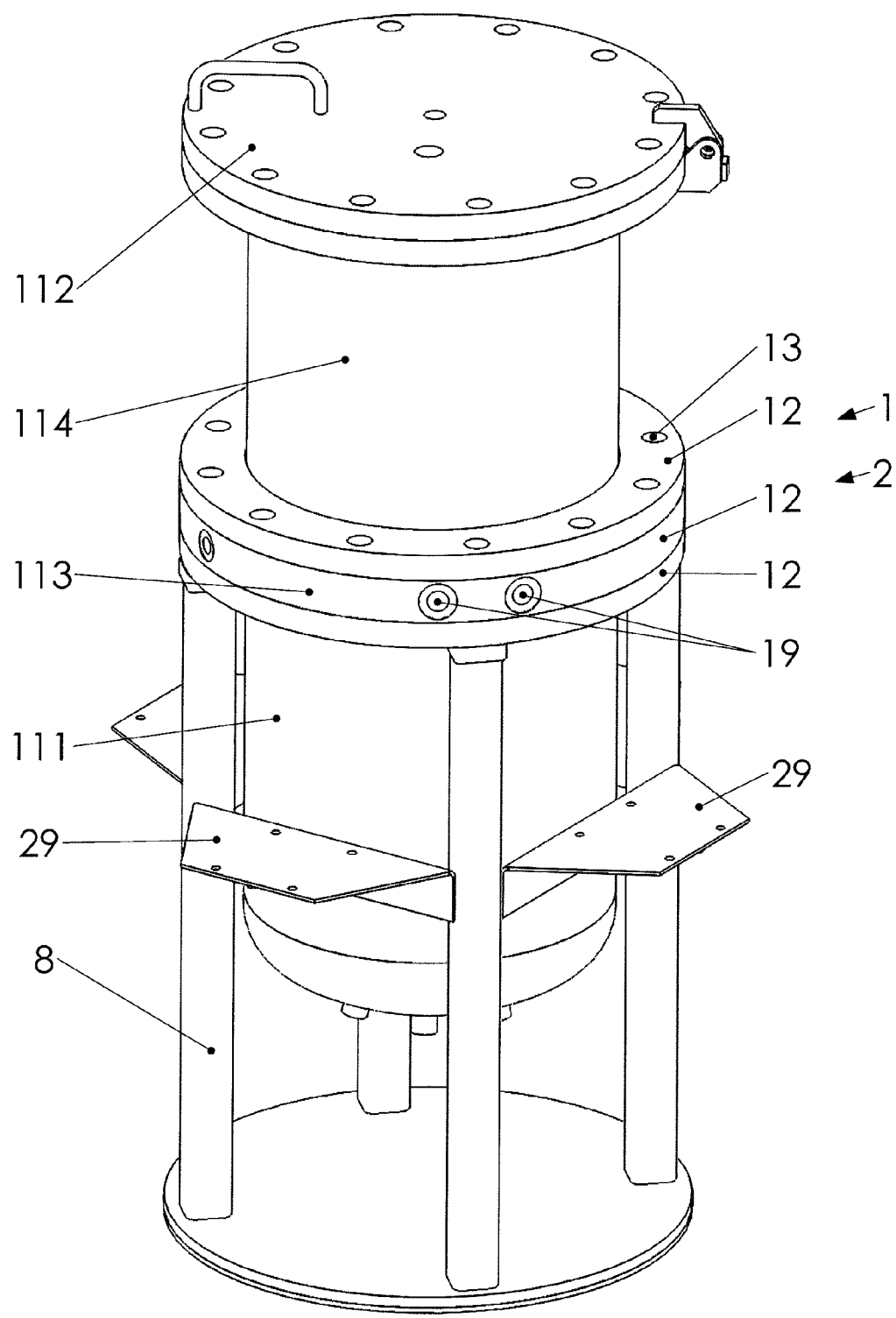
FIG. 5 is a schematic perspective view of fifth example apparatus.

FIG. 5 is a schematic perspective view of fifth example apparatus. This example apparatus is basically similar to that shown in FIG. 3. Now the height of annular section of the vessel 2 created by the heat exchanger module 113 is reduced to consist of a flange structure 12. The flange structure 12 comprises fixing equipment 13 for receiving fixation means that attach the heat exchanger module 113 to a lid module 112 and a motor module 114. Actually, all said modules 112, 113, 114 may be attached to each other by using long bolts etc. that extends through all three flange structures 12. The modules 113 are detachably fixed to each other.

Couplings 19 for conveying heat transfer medium in the heat exchanger 18 (not shown) and out are arranged in the flange structure 12 of the heat exchanger module 113.

Figure 6:
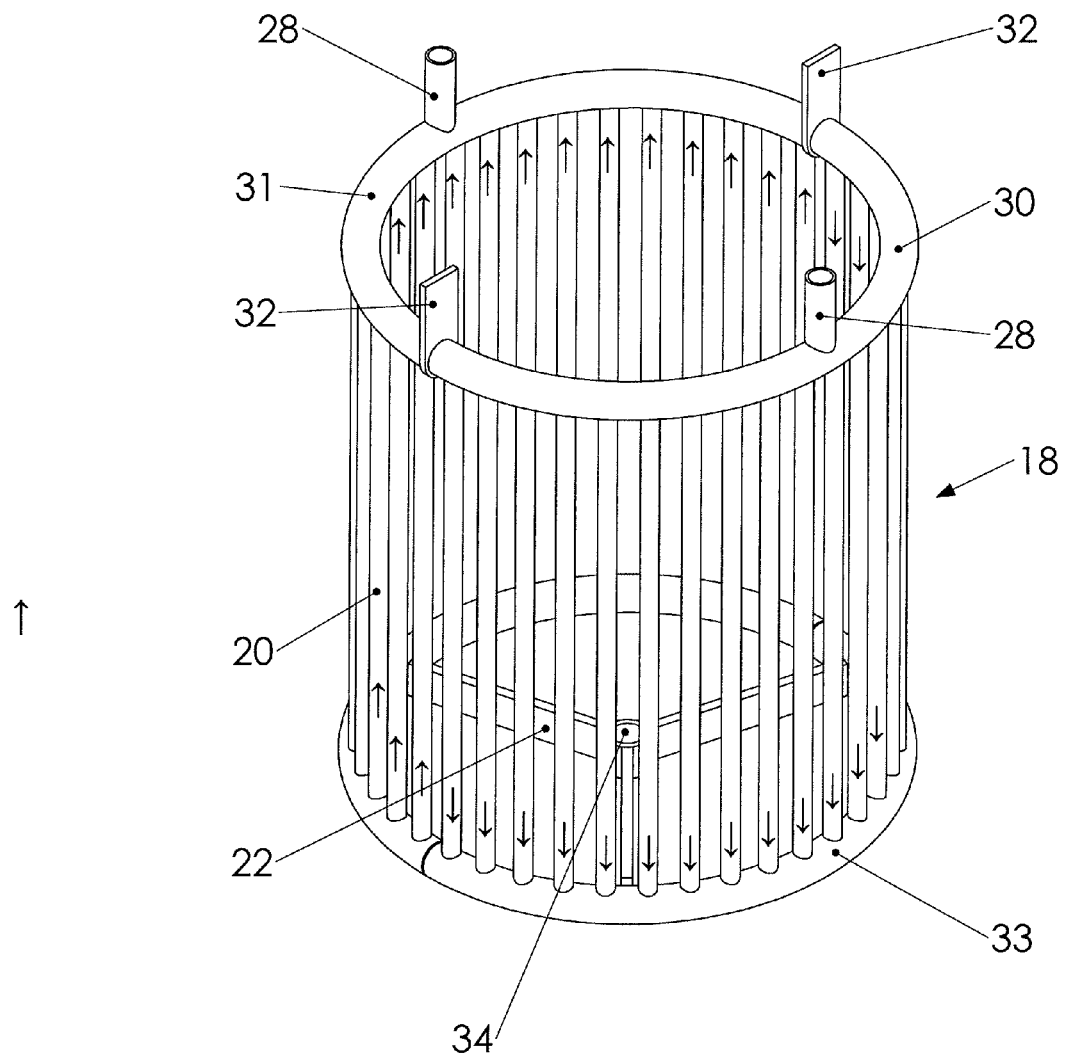
FIG. 6 is a schematic perspective view of sixth example apparatus.

FIG. 6 is a schematic perspective view of an example of a heat exchanger.

The heat exchanger 18 is a tube heat exchanger which comprises heat exchanger tubes 20 through which a heat transfer medium is arranged to flow.

The heat exchanger tubes 20 are arranged vertically and parallel to one another and they may function not only as heat exchange means but also as static baffles.

The heat transfer medium is fed and discharged the tubes 20 by delivery pipes 28. The heat exchanger 18 comprises a feeding delivery manifold 30 arranged to feed the heat transfer medium from the feeding delivery pipe 28 to a feeding portion of the heat exchanger tubes 20. Said feeding portion of the heat exchanger tubes 20 may comprise half of the all heat exchanger tubes 20 of the heat exchanger 18.

Furthermore, the heat exchanger 18 comprises a discharge manifold 31 arranged to receive the heat transfer medium from a discharging portion of the heat exchanger tubes 20. The discharging portion of the heat exchanger tubes 20 comprises rest of the heat exchanger tubes 20, i.e. those heat exchanger tubes 20 which do not belong to the feeding portion of the heat exchanger tubes 20.

The feeding delivery manifold 30 and the discharge manifold 31 are made of a tube that is preferably arranged on top of the heat exchanger 18 where they form a ring as shown in FIG. 6. The manifolds 30, 31 are separated from each other by partition walls 32 which constitute barriers that are impermeable for the heat transfer medium.

On bottom of the heat exchanger 18 there is a connection tube 33 that connects all the heat exchanger tubes 20 so that the heat transfer medium may flow from the feeding portion to the discharging portion of the heat exchanger tubes 20. Arrows in FIG. 6 are showing flowing direction of the heat exchange medium.

An advantage of the heat exchanger 18 shown in FIG. 6 is that its manufacturing costs are quite low. Further advantage is that an uniform heat distribution is easily achieved in the processed matter.

Also in this embodiment the tubes 20 are preferably arranged immediate proximity to the inner surface of the vessel (not shown).

The heat exchanger 18 is preferably detachably fixed in the interior space and attached to a heat exchanger module (not shown). Features of the heat exchanger module are discussed in this description relating to FIG. 3.

A lower mixing means support 34 is arranged at the lower part of the heat exchanger 18. The support 34 may comprise a bearing for supporting a rotating axle in which mixing means are arranged. Thus the rotating axle and mixing means may tolerate very high torsional and/or axial forces caused by e.g. highly viscous matter to be processed. The bearing comprises preferably a conical bearing.

Figure 7:
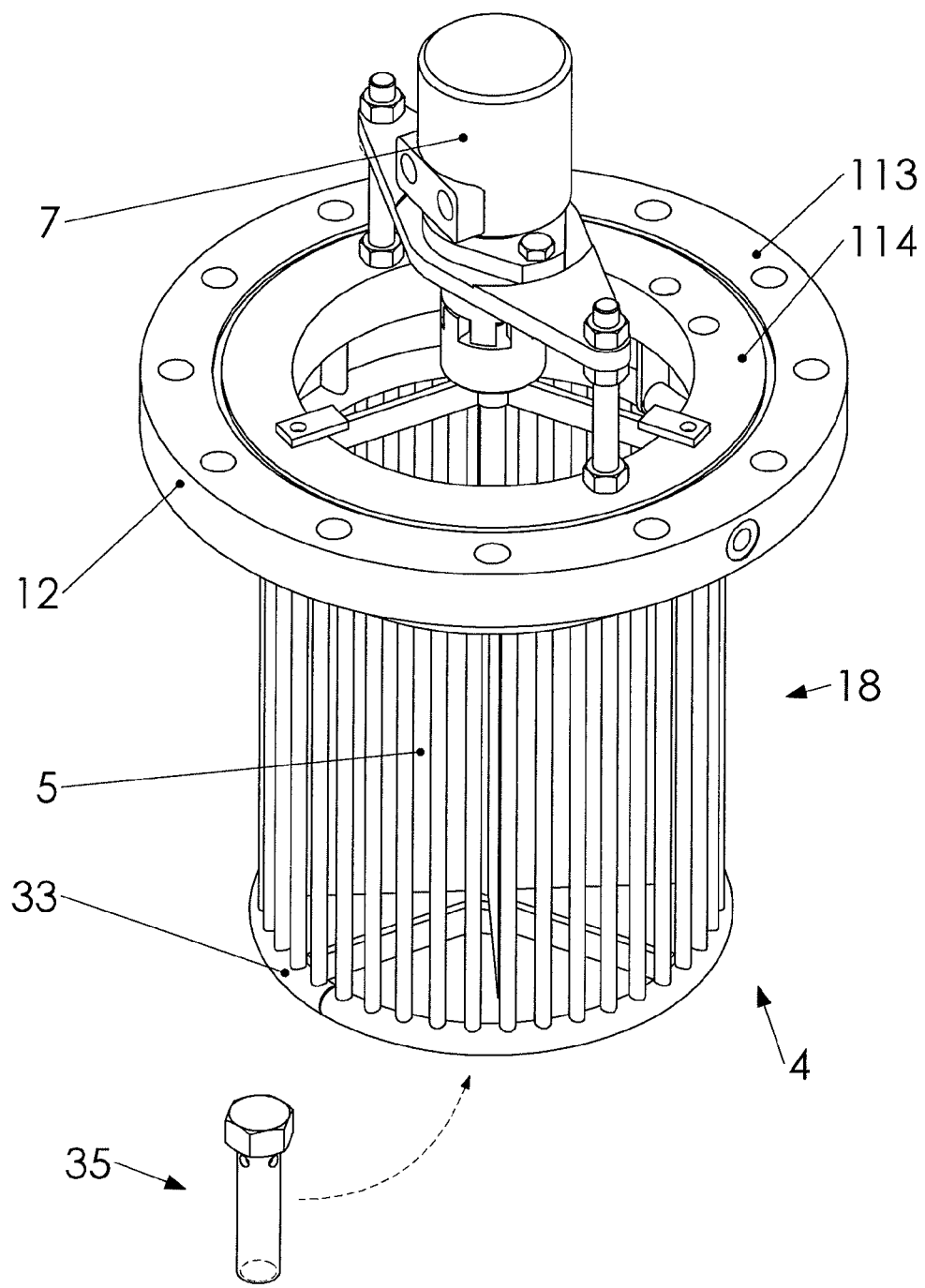
FIG. 7 is a schematic perspective view of seventh example apparatus.

FIG. 7 is a schematic perspective view of an example of a heat exchanger module and an agitation module.

The heat exchanger module 113 comprises a heat exchanger 18 similar to one shown in FIG. 6. The heat exchanger 18 is attached to an exchanger framework 22 which mounts the heat exchanger 18 to a flange structure 12. The heat exchanger module 113 may be used in e.g. bioreactor apparatus 1 shown in FIG. 5.

A motor module 114 is arranged, preferably detachably, to inside the heat exchanger module 113. Thus the motor module 114 does not establish an annular section of the vessel 2 separating interior space 3 from the exterior space. It is to be noted that the vessel 2 and the interior space 3 are not shown in FIG. 7.

An agitation system 4 comprising mixing means 5 and a drive motor 7 is attached to the motor module 114 as discussed earlier in this description.

The mixing means 5 presses or forces the matter to be processed to flow between narrowly arranged heat exchanger tubes 20. This promotes the mixing of the matter and may create a horizontal temperature gradient. The horizontal temperature gradient contributes to more stable and reliable processes taking place in the vessel.

A screen 35 for feeding e.g. gaseous matter may be arranged in the vessel, preferably in the vicinity of the mixing means 5. The screen 35 can be arranged under the mixing means 5 as shown, or above it. The gaseous matter may comprise e.g. $CO_2$ that is used for displacing oxygen from the vessel. The screen 35 may assist mixing of the gaseous matter with matter to be processed.

Figure 8:
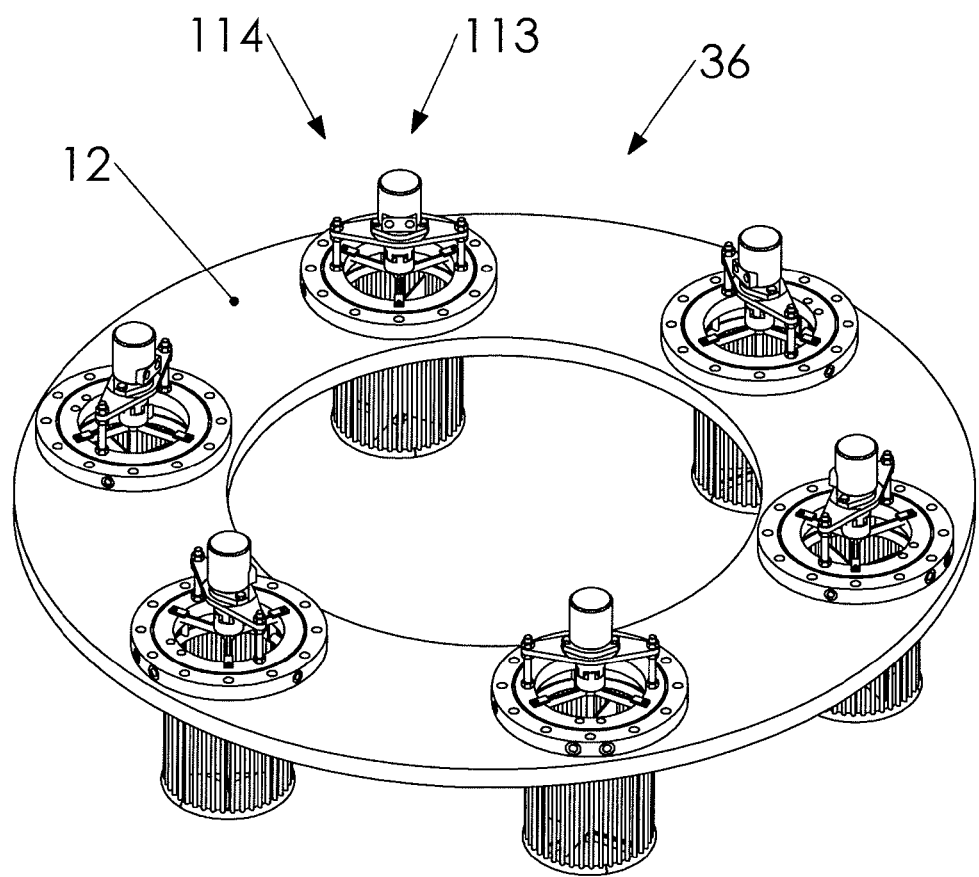
FIG. 8 is a schematic perspective view of eighth example apparatus.

FIG. 8 is a schematic perspective view of an example apparatus. The apparatus may comprise at least two, in FIG. 8 six, exchanger/agitation modules 36. The exchanger/agitation module 36 comprises a heat exchanger module 113 and a motor module 114. Said modules may be e.g. as disclosed in FIG. 7.

The mixing means 5 of the motor module 114 are arranged inside a circumferentially structured heat exchanger 18. The exchanger/agitation module 36 is attached detachably to a flange structure 12 which is attached to the vessel. The flange structure 12 may be a part of the structure of the vessel 2 which separated interior space from the exterior space, but it is not necessary.

In the middle of the flange structure 12 there may be arranged one or more central agitator.

This kind of apparatus is especially suitable for use in vessels capacity of which is 1 m³ or more.

The invention is not limited solely to the embodiments described above, but instead many variations are possible within the scope of the inventive concept defined by the claims below. Within the scope of the inventive concept the attributes of different embodiments and applications can be used in conjunction with or replace the attributes of another embodiment or application.

The drawings and the related description are only intended to illustrate the idea of the invention. The invention may vary in detail within the scope of the inventive idea defined in the following claims.

According to an embodiment, for instance, the inner surface 26 of the vessel may comprise a lining made of different material compared to the vessel 2.

According to another embodiment, the base module 111 may be realized without incorporated bottom wall but, instead, the apparatus comprises a bottom module detachably fixed with the base module 111.

According to still another embodiment, the heat exchanger 18 may be arranged in the bioreactor apparatus 1 shown in FIG. 1. In other words, the heat exchanger 18 may be realized without the heat exchanger module 113.

REFERENCE SYMBOLS 1 bioreactor apparatus
2 vessel
3 interior space
4 agitation system
5 mixing means
6 drive means
7 drive motor
8 support frame
9 temperature controlling means
10 module structure
11 module
12 flange structure
13 fixing equipment
14 aperture
15 lid
16 hinge means
17 hydraulic pump
18 heat exchanger
19 coupling
20 heat exchanger tube
21 fixing element
22 exchanger framework
23 mounting
24 straight tube portion
25 curved tube portion
26 inner surface of the vessel
27 connector
28 delivery pipe
29 attachment element
30 feeding manifold
31 discharge manifold
32 partition wall
33 connection tube
34 lower mixing means support
35 screen
36 exchanger/agitation module
111 base module
112 lid module
113 heat exchanger module
114 motor module
S spacing

What is claimed is:

1. A bioreactor apparatus, comprising:
a vessel establishing an interior space environmentally separable from an exterior space outside of said vessel;
an agitation system comprising mixing means arranged in said interior space and drive means adapted to rotate said mixing means, the drive means comprising a drive motor that is arranged in said interior space and in thermal communication with the interior space such that thermal energy created by the drive motor is used in heating processes or reactions in the interior space;
a heat exchanger detachably fixed in the interior space;
an exchanger framework; and
a heat exchanger module, the heat exchanger being mounted to the exchanger framework, the exchanger framework being detachably fixed in the interior space, the exchanger framework being attached to the heat exchanger module, the heat exchanger module being attached between a base module and a lid module, the heat exchanger module comprising a first flange structure and a second flange structure, the first flange structure and the second flange structure being disposed at opposing ends of the cylindrical section, the heat exchanger module arranged to establish an annular and cylindrical section of the vessel separating the interior space from the exterior space, the heat exchanger module being detachably fixed to a next part of the vessel using the first flange structure, the heat exchanger module being detachably fixed to the base module using the second flange structure.

2. The apparatus as claimed in claim 1, wherein the drive motor is a hydraulic driven motor.

3. The apparatus as claimed in claim 1, wherein the heat exchanger is a tube heat exchanger.

4. The apparatus as claimed in claim 3, wherein the heat exchanger comprises straight or essentially straight tube portions arranged at spacing and parallel to one another and curved tube portions connecting said straight tube portions to form a zigzag tube, the tube portions arranged immediate proximity to the inner surface of the vessel.

5. The apparatus as claimed in claim 4, wherein the straight or essentially straight tube portions are arranged vertically.

6. The apparatus as claimed in claim 4, wherein the straight or essentially straight tube portions are arranged in horizontal direction in the interior space.

7. The apparatus as claimed in claim 1, wherein the agitation system is attached to a motor module that is arranged to establish an annular section of the vessel separating interior space from the exterior space, and that the motor module is detachably fixed to a next part of the vessel.

8. The apparatus as claimed in claim 1, wherein the vessel is gas-tight so that a partial vacuum is allowed to be developed in the interior space.

9. The apparatus as claimed in claim 1, wherein the vessel comprises at least one module having a flange structure arranged on the exterior surface of said vessel, and that said flange structure comprising fixing equipment for receiving fixation means for attachment the module to another part of the vessel.

10. The apparatus as claimed in claim 1, wherein the heat exchanger is constructed to function as static baffles.

11. The apparatus as claimed in claim 1, further comprising temperature controlling means having capability for keeping the temperature of the interior space below 50° C., preferably below 45° C.

12. The apparatus as claimed in claim 1, further comprising a lower mixing means support arranged at the lower part of the heat exchanger 18 for supporting said mixing means.

13. The apparatus as claimed in claim 1, wherein the heat exchanger constitutes a circumferential structure, the heat exchanger comprising a feeding delivery manifold arranged to feed the heat transfer medium to a feeding portion of the heat exchanger tubes, wherein all said tubes are arranged on the same half of the circumferential structure of the heat exchanger.

14. The apparatus as claimed in claim 1, wherein a screen for feeding e.g. gaseous matter is arranged in the vessel in the vicinity of the mixing means.

15. The apparatus as claimed in claim 1, further comprising at least two exchanger/agitation modules each comprising a heat exchanger module and a motor module, wherein the mixing means of the motor module are arranged inside a circumferentially structured heat exchanger.

\* \* \* \* \*

UNITED STATES PATENT AND TRADEMARK OFFICE
CERTIFICATE OF CORRECTION

PATENT NO. : 9,738,862 B2  
APPLICATION NO. : 14/441009  
DATED : August 22, 2017  
INVENTOR(S) : Virtanen et al.

Page 1 of 1

It is certified that error appears in the above-identified patent and that said Letters Patent is hereby corrected as shown below:

In the Specification

Column 3, Line 56:
Now reads: "easily isolated form"
Should read: --easily isolated from--

Signed and Sealed this
Third Day of April, 2018

Andrei Iancu
*Director of the United States Patent and Trademark Office*